US008629083B2

(12) United States Patent
Harrison et al.

(10) Patent No.: US 8,629,083 B2
(45) Date of Patent: Jan. 14, 2014

(54) COMPOSITIONS AND METHODS

(75) Inventors: Steven Harrison, Memphis, TN (US); Bernd Druebbisch, Greensboro, NC (US); Patrick Ewan, Greensboro, NC (US)

(73) Assignee: Syngenta Crop Protection, LLC, Greensboro, NC (US)

( * ) Notice: Subject to any disclaimer, the term of this patent is extended or adjusted under 35 U.S.C. 154(b) by 1263 days.

(21) Appl. No.: 11/914,486

(22) PCT Filed: Jun. 16, 2006

(86) PCT No.: PCT/US2006/023567
§ 371 (c)(1),
(2), (4) Date: Aug. 4, 2008

(87) PCT Pub. No.: WO2007/001919
PCT Pub. Date: Jan. 4, 2007

(65) Prior Publication Data
US 2009/0054237 A1 Feb. 26, 2009

Related U.S. Application Data

(60) Provisional application No. 60/692,858, filed on Jun. 22, 2005.

(51) Int. Cl.
| A01N 43/72 | (2006.01) |
| A01N 43/54 | (2006.01) |
| A01N 43/40 | (2006.01) |
| A01N 43/56 | (2006.01) |
| A01N 37/00 | (2006.01) |
| A01N 47/28 | (2006.01) |

(52) U.S. Cl.
USPC ........... 504/223; 504/243; 504/256; 504/282; 504/307; 504/327

(58) Field of Classification Search
None
See application file for complete search history.

(56) References Cited

U.S. PATENT DOCUMENTS

| 6,518,275 B1 * | 2/2003 | Van Tuyl Cotter et al. ................. 514/258.1 |
| 6,569,809 B1 | 5/2003 | Sato et al. |
| 2002/0035146 A1 | 3/2002 | Young |
| 2008/0039319 A1 * | 2/2008 | Blettner et al. ............... 504/100 |

FOREIGN PATENT DOCUMENTS

| WO | WO-8302546 | * | 8/1983 |
| WO | 2004043150 | | 5/2004 |
| WO | WO-2004057957 | * | 7/2004 |
| WO | 2005/044002 | | 5/2005 |
| WO | 2005044002 | | 5/2005 |

OTHER PUBLICATIONS

Kerby T A: "Cotton Gossypium-Hirsutum Response to Mepiquat Chloride", Agronomy Journal, American Society of Agronomy, Inc. US, vol. 77, No. 4, Jul. 1, 1985, pp. 515-518.
Supplementary European Search Report, European Application EP 06 77 3395, completion date: Jan. 21, 2013.
Grossman K et al: "Bioregulatory effects 1-14 of the fungicidal strobilurin kresoxim-methyl in wheat (*Triticum aestivum*)", Pesticide Science, Elsevier applied Science Publisher, Barking, GB, vol. 50, No. 1, Jan. 1, 1997, pp. 11-20.
Venancio W S et al: "Physiological effects of strobilurin fungicides on plants", Publicatio UEPG. Ciencias Exatas E Da Terra, Ciencias Agrariase Engenharia, Universidade Estadual De Ponta Grossa, Editora, Ponta Grossa, BR, vol. 9, No. 3, Dec. 1, 2013, pp. 59-68.

\* cited by examiner

*Primary Examiner* — Alton Pryor
(74) *Attorney, Agent, or Firm* — R. Kody Jones

(57) ABSTRACT

The present invention relates to mixtures of strobilurin fungicides and plant growth regulators and to the foliar application of these mixtures on crops including cotton.

17 Claims, No Drawings

COMPOSITIONS AND METHODS

This application is a 371 of International Application No. PCT/US2006/023567 filed Jun. 16, 2006, which claims priority to U.S. Ser. No. 60/692,858 filed Jun. 22, 2005, the contents of which are incorporated herein by reference.

BACKGROUND OF THE INVENTION

The present invention relates to mixtures of strobilurin fungicides and plant growth regulators and to the application of these mixtures to crops including the foliar application of these mixtures on cotton.

Disease management in cotton has typically been managed through crop rotation, destruction of plant residue after harvest or application of fungicides in the form of seed treatments or with in-furrow applications. Foliar applications of fungicides on cotton are not currently a common agronomic practice due, in part, to the lack of fungicides registered for this use.

Plant growth regulators (PGRs) are generally any substances or mixtures of substances intended to accelerate or retard the rate of growth or maturation, or otherwise alter the development of plants or their produce. Plant growth regulators (PGRs) affect growth and differentiation of plants. More specifically, various PGRs can, for example, reduce plant height, stimulate seed germination, induce flowering, darken leaf coloring, change the rate of plant growth and modify the timing and efficiency of fruiting.

PGRs are recognized as an essential tool in modern cotton production. Mepiquat (IUPAC name: N,N-dimethylpiperidinium) is a widely accepted PGR for cotton plants and is typically applied to cotton plants in the form of a salt, such as mepiquat chloride or mepiquat pentaborate, by foliar application. U.S. Pat. Nos. 5,478,796; 5,627,134; 5,650,372; 5,654,255; 5,869,424; 5,935,906; 6,224,734; 6,232,270; 6,248,694; 6,288,009; 6,376,425 and 6,465,394 teach various mepiquat formulations and their use in cotton.

SUMMARY OF THE INVENTION

The present invention relates to mixtures of strobilurin fungicides and plant growth regulators and to the application of these mixtures to crops including the foliar application of these mixtures on cotton.

In one embodiment, the mixtures of the present invention allow for the foliar application of both a fungicide and a plant growth regulator resulting in improvements in cotton production such as improved plant health, increased cotton yield and/or improved fiber quality even in the absence of obvious disease pressure.

DETAILED DESCRIPTION OF THE INVENTION

The fungicides used in the mixtures of present invention comprise at least one strobilurin fungicide preferably at least one strobilurin fungicide selected from the group consisting of azoxystrobin, dimoxystrobin, fluoxastrobin, kresoxim-methyl, metominostrobin, orysastrobin, picoxystrobin, pyraclostrobin and trifloxystrobin.

Plant growth regulators are any substances or mixtures of substances intended to alter the germination, growth, maturation, or development of plants or their produce. Plant growth regulators may be classified into subcategories including, but not limited to antiauxins (such as clofibric acid, 2,3,5-tri-iodobenzoic acid), auxins (such as 4-CPA, 2,4-D, 2,4-DB, 2,4-DEP, dichlorprop, fenoprop, IAA, IBA, naphthaleneacetamide, α-naphthaleneacetic acid, 1-naphthol, naphthoxyacetic acid, potassium naphthenate, sodium naphthenate, 2,4,5-T), cytokinins (such as 2iP, benzyladenine, kinetin, zeatin), defoliants (such as calcium cyanamide, dimethipin, endothal, ethephon, merphos, metoxuron, pentachlorophenol, thidiazuron, tribufos), ethylene inhibitors (such as aviglycine, 1-methylcyclopropene), ethylene releasers (such as ACC, etacelasil, ethephon, glyoxime), gibberellins (such as gibberellins, gibberellic acid), growth inhibitors (such as abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham, 2,3,5-tri-iodobenzoic acid), morphactins (such as chlorfluren, chlorflurenol, dichlorflurenol, flurenol), growth retardants/modifiers (such as chlormequat, daminozide, flurprimidol, mefluidide, paclobutrazol, cyproconazole, tetcyclacis, uniconazole), growth stimulators (such as brassinolide, forchlorfenuron, hymexazol, 2-amino-6-oxypurine derivatives, indolinone derivates, 3,4-disubstituted maleimide derivatives and fused azepinone derivatives). The term additionally includes other active ingredients such as benzofluor, buminafos, carvone, ciobutide, clofencet, cloxyfonac, cyclanilide, cycloheximide, epocholeone, ethychlozate, ethylene, fenridazon, heptopargil, holosulf, inabenfide, karetazan, lead arsenate, methasulfocarb, prohexadione, pydanon, sintofen, triapenthenol, and trinexapac-ethyl Preferred plant growth regulators include growth retardants, gibberellins, growth inhibitors, and growth stimulators. Particularly preferred plant growth regulators include growth retardants, such as paclobutrazol, cyproconazole, flurprimidol, and uniconazole.

The plant growth regulators (PGRs) used in the mixtures of the present invention preferably comprise at least one member selected from the group consisting of mepiquat and salts thereof, such as mepiquat chloride or mepiquat pentaborate, and chloromequat chloride, flurprimidol, paclobutrazol, uniconazole, ancymidol, trinexapac-ethyl, prohexadione-Ca and daminozide. The selection of PGR can be influenced by the intended crop. Of the compounds noted above, when the crop is cotton, PGRs comprising mepiquat chloride and/or mepiquat pentaborate are preferred.

These compounds are known in the art and are described in The Pesticide Manual, Twelfth Edition, British Crop Protection Council or other readily available resources.

Commercially available mepiquat chloride containing products suitable for use in the present invention include MEPEX® plant regulator and MEPEX® PLUS plant growth regulator both available from Griffin Corporation, DuPont™ MEPEX® GIN OUT™ plant growth regulator available from E.I. DuPont de Nemours, PIX® Plus plant regulator and PIX® Ultra plant regulator both available from BASF Corporation and Mepichlor 4.2% Liquid available from Micro Flo Company. STANCE™ SC Plant Regulator available from Bayer Crop Science comprises a mixture of mepiquat chloride and cyclanilide. PENTIA™ plant regulator available from BASF Corporation is an example of a commercially available mepiquat pentaborate containing formulation suitable for use in the present invention.

While there is no particular limitation to the crops where these mixtures can be used, preferred crops include apples, cereals, cotton, ornamentals, peanuts and turf.

In one embodiment, the mixtures of the present invention are preferably applied to the foliage of cotton plants. Multiple applications of the strobilurin fungicide and/or the plant growth regulator may be required or desired. In one embodiment, the strobilurin fungicide is applied to the cotton plant from first pinhead square to first bloom. Preferably, the first application of the fungicide or the mixtures of the present invention to the foliage of the cotton plants is from first pinhead square to first bloom. Subsequent applications of the mixtures of the present invention or of the fungicide or plant growth regulator, separately, may be made as needed. If subsequent applications are used, applications are preferably timed at approximately 10 to 21 days apart. The timing of first pin-head square and first bloom as well as the timing for the first application of the plant growth regulator and the need for subsequent applications of a fungicide and/or a plant growth regulator will vary based on numerous factors including region, climate, pest pressure and variety of cotton and can readily be determined by one skilled in cotton production.

The term "crops" is to be understood as including also crops that have been rendered tolerant to herbicides like bromoxynil, dicamba, paraquat or classes of herbicides (such as, for example, PPO inhibitors, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

Herbicide-resistant cotton varieties, such as glyphosate, glufosinate and bromoxynil resistant cotton are commercially-available, widely used and described in readily available resources.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP) e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). Truncated toxins, for example a truncated CryIA(b), are known. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: NuCOTN 33B® (cotton variety that expresses a CryIA(c) toxin); Bollgard J® (cotton variety that expresses a CryIA(c) toxin); Bollgard II® (cotton variety that expresses a CryIA(c) and a CryIIA(b) toxin); VIPCOT® (cotton variety that expresses a VIP toxin).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

In addition to the expression of toxins, for example toxins from *Bacillus thuringiensis* (Bt) for insect resistance, the transgenic cotton plants may also include other transgenic properties, for example further insect resistance, herbicide resistance such as resistance to herbicides including bromoxynil, glyphosate or glufosinate, or resistance to nematodes, fungi or viruses, or may be genetically modified in their metabolic properties resulting in a qualitative and/or quantitative change of ingredients (for example by modification of the energy, carbohydrate, fatty acid or nitrogen metabolism or by metabolite streams which influence these).

One embodiment of the present invention comprises a concentrate comprising at least one strobilurin fungicide and at least plant growth regulator. Prior to application, the concentrate is diluted in a suitable carrier, such as water, in, for example, a spray tank.

In one embodiment, the present invention is directed to a composition comprising a) at least one strobilurin fungicide and b) at least one plant growth regulator wherein the composition is obtained by combining, for example in a spray tank, a strobilurin fungicide, preferably a formulated composition comprising at least one strobilurin fungicide and a plant growth regulator, preferably a formulated composition comprising at least one plant growth regulator.

The term "formulated composition" as used herein means compositions, preferably concentrates, comprising at least one fungicide or plant growth regulator and other formulations components such as surfactants, adjuvants, stabilizers and the like. Formulated compositions include commercially available pre-mixes that can be used upon dilution in a spray tank or tank mixed with other formulated compositions, other pesticidally active ingredients, adjuvants, fertilizers and the like.

One embodiment of the present invention is directed to a method of treating crops comprising applying a mixture comprising at least one strobilurin fungicide and at least one plant growth regulator to the foliage of said crop.

One embodiment of the present invention is directed to a method of treating cotton plants comprising applying a mixture comprising at least one strobilurin fungicide and at least one plant growth regulator to the foliage of said cotton plant.

The invention relates also to a method for improving yield and/or fiber quality in crops of cotton plants, said method comprising forming applying a mixture of at least one strobilurin fungicide and at least one plant growth regulator in a suitable carrier, such as water, to the foliage of said cotton plants.

The invention relates also to a method for improving yield and/or fiber quality in crops of cotton plants, said method comprising forming a composition by i) diluting a concentrate containing a mixture of at least one strobilurin fungicide and at least one plant growth regulator in a suitable carrier, such as water, such that the final concentration of each of the strobilurin fungicide and plant growth regulator is between about 0.01% and about 30% of active ingredient (a.i.) and ii) applying said composition to the foliage of the cotton plants.

The invention relates also to a method for improving yield and/or fiber quality in crops of cotton plants, said method comprising forming a composition by i) diluting, in a vessel such as a spray tank, a concentrate containing at least one strobilurin fungicide and a concentrate containing at least one plant growth regulator in a suitable carrier, such as water, such that the final concentration of each of the strobilurin fungicide and plant growth regulator is between about 0.01% and about 30% of active ingredient (a.i.) and ii) applying said composition to the foliage of the cotton plants.

The benefits obtained by applying the compositions of the present invention to the foliage of the crops can be recognized even in the absence of an agronomically significant level of pest pressure by fungal plant pathogens.

The components used in the composition of the invention can be applied to the foliage of the cotton plants in a variety of ways known to those skilled in the art and at various concentrations. The rate at which the compositions are applied will depend upon, among other things, the degree of control required and the timing and method of application.

Other active ingredients such as herbicides, additional plant growth regulators, additional fungicides, insecticides, acaricides and nematicides may be present in the concentrates of the present invention or may be added as a tank-mix partner with the strobilurin fungicide and the plant growth regulator. Further, these other active ingredients may be applied to the seeds, plants, plant locus or plant propagation material prior or subsequently to the application of the compositions of the present invention.

We claim:

1. A method for improving yield and/or fiber quality in crops of cotton plants, said method comprising:
   forming a composition by diluting a concentrate containing a mixture of at least one strobilurin fungicide selected from azoxystrobin, dimoxystrobin, fluoxastrobin, kresoxim-methyl, metaminostrobin, orysastrobin, pyraclostrobin and trifloxystrobin and at least one plant growth regulator in a carrier such that the final concentration of each of the strobilurin fungicide and the plant growth regulator is independently between about 0.01% and about 30% of active ingredient, and
   applying the composition to the foliage of the cotton plants, wherein the application occurs from first pinhead square to first bloom of the cotton plants.

2. The method of claim 1 wherein the composition is applied to the foliage of the cotton plants in the absence of an agronomically significant level of pest pressure by fungal plant pathogens.

3. The method of claim 1 wherein the strobilurin fungicide comprises azoxystrobin, and the plant growth regulator comprises mepiquat chloride.

4. The method of claim 1 wherein the strobilurin fungicide comprises at least one member selected from the group consisting of azoxystrobin, kresoxim-methyl, picoxystrobin, pyraclostrobin and trifloxystrobin.

5. The method of claim 4 wherein the strobilurin fungicide comprises azoxystrobin.

6. The method of claim 1 wherein the plant growth regulator comprises at least one member selected from the group consisting of antiauxins, auxins, cytokinins, defoliants, ethylene inhibitors, ethylene releasers, gibberellins, growth inhibitors, morphactins, growth retardants/modifiers, growth stimulators, benzofluor, buminafos, carvone, ciobutide, clofencet, cloxyfonac, cyclanilide, cycloheximide, epocholeone, ethychlozate, ethylene, fenridazon, heptopargil, holosulf, inabenfide, karetazan, lead arsenate, methasulfocarb, prohexadione, pydanon, sintofen, triapenthenol and trinexapac.

7. The method of claim 6 wherein the plant growth regulator comprises at least one member selected from the group consisting of clofibric acid; 2,3,5-tri-iodobenzoic acid; 4-CPA; 2,4-D; 2,4-DB; 2,4-DEP; dichlorprop; fenoprop; IAA; IBA; naphthaleneacetamide; α-naphthaleneacetic acid; 1-naphthol; naphthoxyacetic acid; potassium naphthenate; sodium naphthenate; 2,4,5-T; 2iP; benzyladenine; kinetin; zeatin; calcium cyanamide; dimethipin; endothal; ethephon; merphos; metoxuron; pentachlorophenol; thidiazuron; tributos; aviglycine; 1-methylcyclopropene; ACC; etacelasil; ethephon; glyoxime; gibberellins; gibberellic acid; abscisic acid; ancymidol; butralin; carbaryl; chlorphonium; chlorpropham; dikegulac; flumetralin; fluoridamid; fosamine; glyphosine; isopyrimol; jasmonic acid; maleic hydrazide; mepiquat and salts thereof; piproctanyl; prohydrojasmon; propham; 2,3,5-tri-iodobenzoic acid; chlorfluren; chlorflurenol; dichlorflurenol; flurenol; chlormequat; daminozide;

flurprimidol; mefluidide; paclobutrazol; cyproconazole; tetcyclacis; uniconazole; brassinolide; forchlorfenuron; hymexazol; indolinone derivates; 3,4-disubstituted maleimide derivatives; fused azepinone derivatives; benzofluor; buminafos; carvone; ciobutide; clofencet; cloxyfonac; cyclanilide; cycloheximide; epocholeone; ethychlozate; ethylene; fenridazon; heptopargil; holosulf; inabenfide; karetazan; lead arsenate; methasulfocarb; prohexadione; pydanon; sintofen; triapenthenol; and trinexapac-ethyl.

8. The method of claim 7 wherein the plant growth regulator comprises at least one member selected from the group consisting of mepiquat and salts thereof, mepiquat chloride, mepiquat pentaborate, chloromequat chloride, flurprimidol, paclobutrazol, uniconazole, ancymidol, trinexapac-ethyl, prohexadione-Ca and daminozide.

9. The method of claim 8 wherein the plant growth regulator comprises mepiquat and salts thereof.

10. The method of claim 9 wherein the plant growth regulator comprises at least one member selected from the group consisting of mepiquat chloride and mepiquat pentaborate.

11. The method of claim 1 wherein the strobilurin fungicide comprises azoxystrobin, and the plant growth regulator comprises at least one member selected from the group consisting of mepiquat chloride and mepiquat pentaborate.

12. The method of claim 2 wherein the strobilurin fungicide comprises azoxystrobin, and the plant growth regulator comprises at least one member selected from the group consisting of mepiquat chloride and mepiquat pentaborate.

13. A method for improving yield and/or fiber quality in crops of cotton plants, said method comprising:

forming a composition by diluting in a vessel a first concentrate containing at least one strobilurin fungicide selected from azoxystrobin, dimoxystrobin, fluoxastrobin, kresoxim-methyl, metaminostrobin, orysastrobin, pyraclostrobin and trifloxystrobin and a second concentrate containing at least one plant growth regulator in a carrier such that the final concentration of each of the strobilurin fungicide and plant growth regulator is independently between about 0.01% and about 30% of active ingredient (a.i.), and applying the composition to the foliage of the cotton plants, wherein the application occurs from first pinhead square to first bloom of the cotton plants.

14. The method of claim 13 wherein the strobilurin fungicide comprises azoxystrobin, and the plant growth regulator comprises at least one member selected from the group consisting of mepiquat chloride and mepiquat pentaborate.

15. The method of claim 13 wherein the composition is applied to the foliage of the cotton plants in the absence of an agronomically significant level of pest pressure by fungal plant pathogens.

16. The method of claim 15 wherein the strobilurin fungicide comprises azoxystrobin, and the plant growth regulator comprises at least one member selected from the group consisting of mepiquat chloride and mepiquat pentaborate.

17. The method of claim 16 wherein the strobilurin fungicide comprises azoxystrobin, and the plant growth regulator comprises mepiquat chloride.

* * * * *